United States Patent
Iketani et al.

(10) Patent No.: US 7,877,135 B2
(45) Date of Patent: Jan. 25, 2011

(54) IMAGE DATA PROCESSOR, COMPUTER PROGRAM PRODUCT, AND ELECTRONIC ENDOSCOPE SYSTEM

(75) Inventors: Kohei Iketani, Saitama (JP); Mitsufumi Fukuyama, Saitama (JP)

(73) Assignee: Hoya Corporation, Tokyo (JP)

( * ) Notice: Subject to any disclaimer, the term of this patent is extended or adjusted under 35 U.S.C. 154(b) by 1126 days.

(21) Appl. No.: 11/352,228

(22) Filed: Feb. 13, 2006

(65) Prior Publication Data
US 2006/0241498 A1 Oct. 26, 2006

(30) Foreign Application Priority Data
Feb. 16, 2005 (JP) .......................... P2005-039029

(51) Int. Cl.
*A61B 6/00* (2006.01)
(52) U.S. Cl. ..................... 600/476; 600/473; 600/321; 600/329
(58) Field of Classification Search ............... 600/476, 600/478, 423, 467, 473; 356/317–18
See application file for complete search history.

(56) References Cited

U.S. PATENT DOCUMENTS

| 6,638,215 | B2 * | 10/2003 | Kobayashi | 600/160 |
|---|---|---|---|---|
| 6,796,938 | B2 | 9/2004 | Sendai | |
| 6,930,706 | B2 | 8/2005 | Kobayashi et al. | |
| 2002/0026098 | A1 * | 2/2002 | Kobayashi | 600/160 |
| 2002/0161282 | A1 * | 10/2002 | Fulghum | 600/160 |
| 2002/0176009 | A1 * | 11/2002 | Johnson et al. | 348/229 |
| 2003/0078477 | A1 | 4/2003 | Kang et al. | |
| 2004/0242962 | A1 | 12/2004 | Uchiyama | |
| 2005/0288553 | A1 | 12/2005 | Sugimoto | |
| 2005/0288556 | A1 | 12/2005 | Sugimoto | |
| 2006/0020169 | A1 | 1/2006 | Sugimoto | |
| 2007/0073106 | A1 | 3/2007 | Uchiyama | |

FOREIGN PATENT DOCUMENTS

| JP | 61-048333 | 3/1986 |
|---|---|---|
| JP | 63-220837 | 9/1988 |

(Continued)

OTHER PUBLICATIONS

U.S. Appl. No. 11/329,103 to Fukuyama, which was filed on Jan. 11, 2006.

(Continued)

*Primary Examiner*—Long V Le
*Assistant Examiner*—Joel F Brutus
(74) *Attorney, Agent, or Firm*—Greenblum & Bernstein P.L.C.

(57) ABSTRACT

An image data processor comprising an image signal receiver, a histogram generator, a gain calculator, an amplifier, and a signal feeder, is provided. The image signal receiver receives an autofluorescence image signal. The autofluorescence image signal is generated by an imaging device when the imaging device captures an autofluorescence image. The histogram generator generates a histogram of luminance in the autofluorescence image based on the autofluorescence image signal. The gain calculator calculates a gain based on the histogram and a predetermined luminance value. The amplifier amplifies the autofluorescence image signal by the gain. And then the amplifier generates an amplified autofluorescence image signal. The signal feeder outputs the amplified autofluorescence image signal to a monitor. The monitor displays an amplified autofluorescence image.

20 Claims, 9 Drawing Sheets

FOREIGN PATENT DOCUMENTS

| | | |
|---|---|---|
| JP | 1-277532 | 11/1989 |
| JP | 2001-149303 | 6/2001 |
| JP | 2002-094979 | 3/2002 |
| JP | 2002-102147 | 4/2002 |
| JP | 2003-10101 | 1/2003 |
| JP | 2003-010101 | 1/2003 |
| JP | 2003-033324 | 2/2003 |
| JP | 2003-204924 | 7/2003 |
| JP | 2004-350963 | 12/2004 |

OTHER PUBLICATIONS

English language Abstract of JP 2003-10101.

* cited by examiner

IMAGE DATA PROCESSOR, COMPUTER PROGRAM PRODUCT, AND ELECTRONIC ENDOSCOPE SYSTEM

BACKGROUND OF THE INVENTION

1. Field of the Invention

The present invention relates to an image data processor and an electronic endoscope system which carries out a specific image process on image signals generated by an autofluorescence endoscope.

2. Description of the Related Art

It is known that an organ generates autofluorescence when the organ is illuminated by exciting light having a specific wavelength, for example ultraviolet light. It is also known that an amount of autofluorescence at, for example, a cancerous region, is less than that of a healthy area in an organ. An autofluorescence endoscope system taking advantage of the above properties has been invented. The autofluorescence endoscope system usually has a reference light source for emitting white light, an exciting light source for emitting exciting light, and a monitor. A reference image is displayed on the monitor when an object is illuminated by the white light. An autofluorescence image is displayed on the monitor when the object is illuminated by the exciting light.

Further, it is prohibited to irradiate strong exciting light to an organ from a medical point of view. An autofluorescence image, irradiated with a limited amount of exciting light, is too dark to observe. Accordingly, it is difficult for a user to make a diagnosis utilizing an autofluorescence image.

SUMMARY OF THE INVENTION

Therefore, an object of the present invention is to provide an image data processor and an electronic endoscope system so that an adequately bright autofluorescence image is automatically displayed.

According to the present invention, an image data processor comprising an image signal receiver, a histogram generator, a gain calculator, an amplifier, and a feeder, is provided. The image signal receiver receives an autofluorescence image signal. The autofluorescence image signal is generated by an imaging device when the imaging device captures an autofluorescence image. The autofluorescence image is an optical image of an object illuminated by an exciting light. The exciting light makes an organ generate autofluorescence. The histogram generator generates an autofluorescence histogram of luminance in the autofluorescence image based on the autofluorescence image signal. The gain calculator calculates an autofluorescence gain based on the autofluorescence histogram and a predetermined luminance value for the autofluorescence image signal. The autofluorescence gain is used for amplifying the autofluorescence image signal. The amplifier amplifies the autofluorescence image signal by the autofluorescence gain. And then the amplifier generates an amplified autofluorescence image signal. The signal feeder can output the amplified autofluorescence image signal to a monitor. The monitor displays an amplified autofluorescence image. The amplified autofluorescence image corresponds to the amplified autofluorescence image signal.

Further preferably, the autofluorescence gain is calculated so that a maximum luminance value in the autofluorescence histogram amplified by the autofluorescence gain agrees with the predetermined luminance value. Or the autofluorescence gain is calculated so that an average luminance value in said histogram amplified by the autofluorescence gain agrees with the predetermined luminance value.

Further preferably, when the imaging device is mounted in an electronic endoscope, the predetermined luminance value is decided according to the properties of the electronic endoscope connected to the image data processor.

Further preferably, the image data processor comprises an input unit for fine manual adjustment of the autofluorescence gain calculated by the gain controller.

BRIEF DESCRIPTION OF THE DRAWINGS

The objects and advantages of the present invention will be better understood from the following description, with reference to the accompanying drawings in which:

FIG. 6 is a timing chart to explain a timing to illuminate reference light or exciting light, to carry out the auto gain control process, and so on;

DESCRIPTION OF THE PREFERRED EMBODIMENTS

The present invention is described below with reference to the embodiment shown in the drawings.

Figure 1:
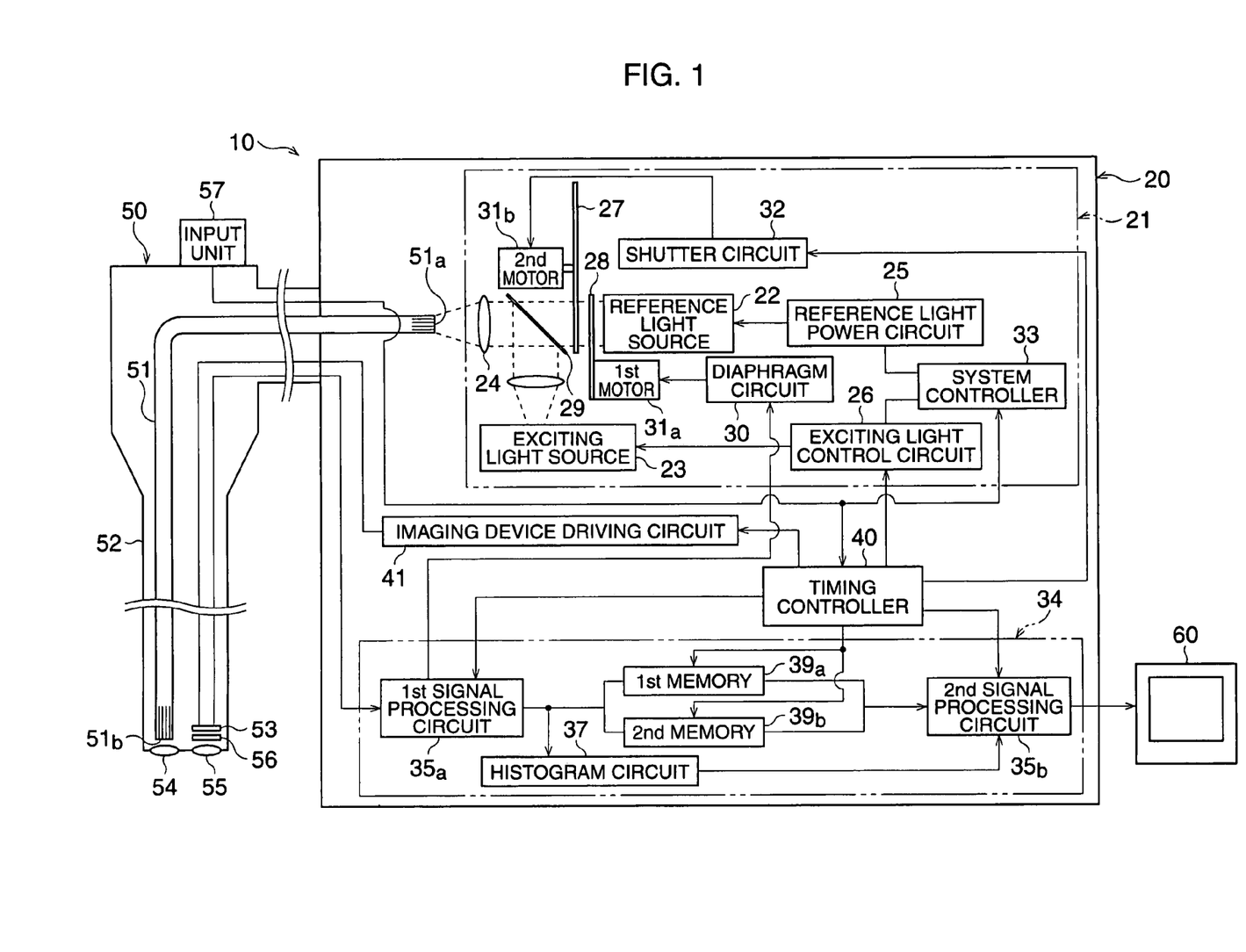
FIG. 1 is a block diagram showing the internal structure of an electronic endoscope system having an image data processor of an embodiment of the present invention.

In FIG. 1, an electronic endoscope system 10 comprises an endoscope processor 20, an endoscope 50, and a monitor 60. The endoscope processor 20 is connected to the endoscope 50 and the monitor 60.

A light system 21 is housed in the endoscope processor 20. The light system 21 emits light to illuminate a required object. The light, that the light system emits, is transmitted by the light guide 51 housed in the endoscope 50. And the required object is illuminated by the transmitted light.

The endoscope 50 comprises an imaging device 53, such as a CCD, at the head end of an insert tube 52. The imaging device 53 captures an optical image of the required object. The imaging device 53 generates image signals corresponding to the captured image. The image signal is sent to the endoscope processor 20. The endoscope processor 20 comprises an image process system 34. The image process system 34 carries out some predetermined signal processes for the image signals. The image process system 34 can carry out an auto gain control process, referred to as AGC process, described in detail later. The predetermined signal processes include not only the AGC process but also the usual signal processes, such as a gamma process, white balance process, and so on. The image signal, being carried out the predetermined processes, is sent to the monitor 60. An image, corresponding to the image signal sent to the monitor 60, is displayed on the monitor 60.

The light system 21 comprises a reference light source 22, an exciting light source 23, condenser lens 24, a reference light power circuit 25, an exciting light control circuit 26, shutter 27, diaphragm 28, and so on.

A reference light source 22 emits reference light, such as white light. An exciting light source 23 emits exciting light, such as ultraviolet light, having a specific wavelength.

The diaphragm 28, shutter 27, dichroic mirror 29, and the condenser lens 24 are mounted in an optical path of the reference light emitted by the reference light source 22 to the incident end 51a of the light guide 51. The reference light, which is almost all parallel light beams, is made incident on the incident end 51a, through the dichroic mirror 29 and the condenser lens 24. The condenser lens 24 condenses the reference light for the incident end 51a.

A reference light intensity is adjusted by driving the diaphragm 28. A first motor 31a, controlled by the diaphragm circuit 30, drives the diaphragm 28. The diaphragm circuit 30 is connected to a first signal processing circuit 35a. The first signal processing circuit 35a detects the luminance of the object based on the image signals generated by the imaging device 53. The diaphragm circuit 30 calculates a driving quantity of the first motor 31a based on the detected luminance of the object and a preset luminance.

Figure 2:
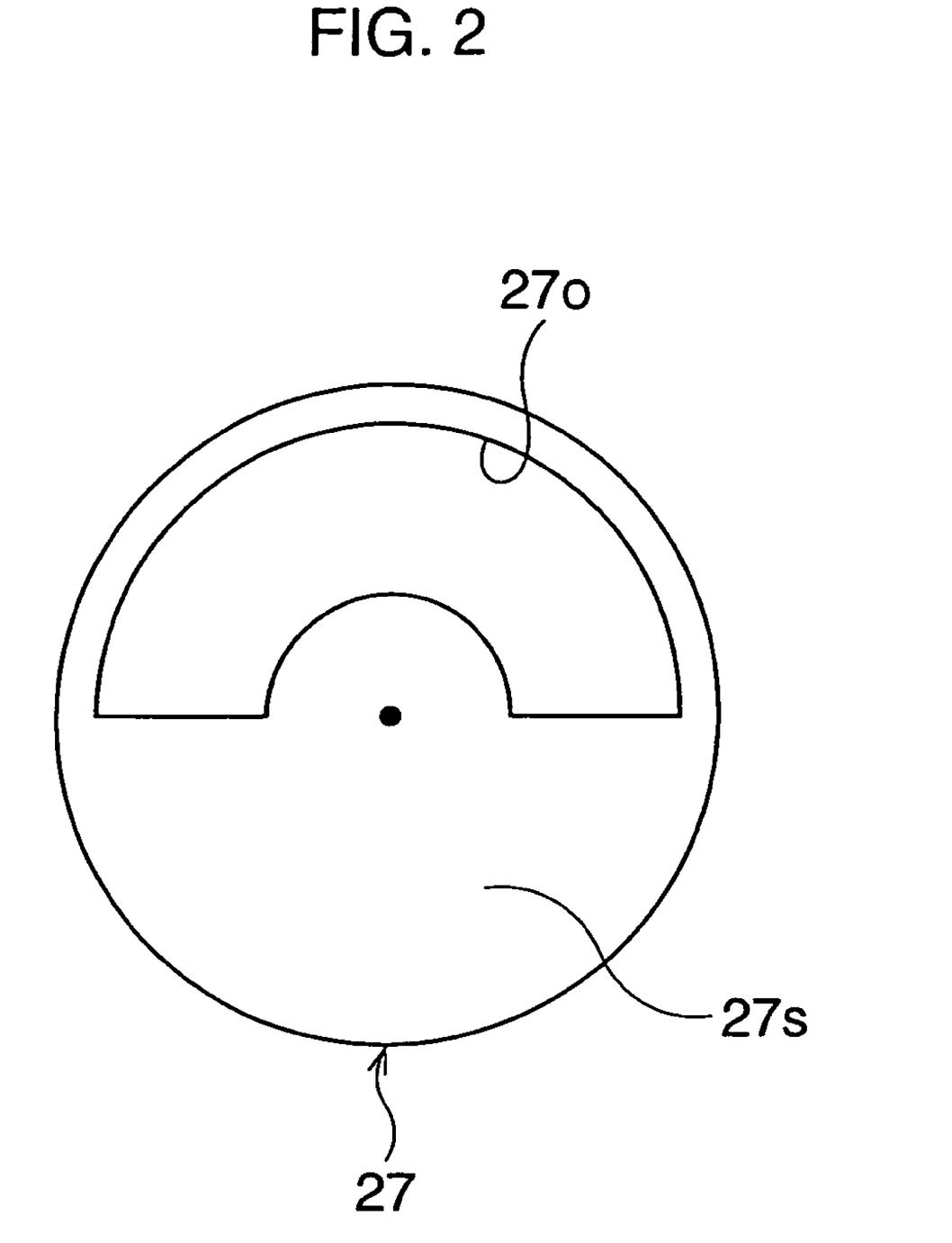
FIG. 2 is a plan of the shutter.

The shutter 27 is a rotary shaped shutter as shown in FIG. 2. Passing through or shielding the reference light is changed by driving the shutter 27. The shutter 27 has an aperture 27o and a shielding plate 27s. The aperture 27o is inserted into the optical path of the reference light when the reference light is controlled to pass through the optical path. The shielding plate 27s is inserted into the optical path of the reference light when the reference light is shielded. A second motor 31b, controlled by a shutter circuit 32, drives the shutter 27.

The exciting light beams emitted by the exciting light source 23 are made almost all parallel. The exciting light source 23 is mounted so that the exciting light beams, that are made almost all parallel, are incident on the incident end 51a after being reflected by the dichroic mirror 29. For example, when an exciting light source 23 is set up so that an angle between the optical paths of the reference light and the exciting light is 90 degrees, the dichroic mirror 29 is mounted at an angle of 45 degrees between a plane of the dichroic mirror 29 and the optical path of the reference light. The exciting light control circuit 26 controls the switching of the exciting light source 23 on and off.

The shutter circuit 32 and the exciting light control circuit 26 are connected to a timing controller 40. The timing controller 40 outputs a shutter timing signal to the shutter circuit 32. The shutter timing signal controls an amount of time the reference light passes through the shutter 27, and an amount of time the reference light is shielded. Further, the timing controller 40 outputs an emission timing signal to the exciting light control circuit 26. The emission timing signal controls a timing to switch the exciting light source 23 on and off.

The timing controller 40 outputs the shutter timing signal and the emission timing signal so that the exciting light source 23 is switched off when the reference light is controlled to pass through the shutter 27. The timing controller 40 outputs the shutter timing signal and the emission timing signal so that the exciting light source 23 is switched on when the reference light is shielded by the shutter 27. Accordingly, changing the light to illuminate the required object is carried out by an operation of the timing controller 40, the exciting light control circuit 26, the shutter circuit 32, the second motor 31b, and the shutter 27.

Further, the timing controller 40 outputs a necessary timing signal for driving the imaging device 53, to an imaging device driving circuit 41. Further still, the timing controller 40 is connected to the image process system 34, and the timing controller 40 outputs another timing signal, described later, to the image process system 34.

Power for the reference light source 22 is supplied by the reference light power circuit 25. The reference light power circuit 25 and the exciting light control circuit 26 are connected to a system controller 33. The system controller 33 is connected to an input unit 57 mounted on the endoscope 50. The input unit 57 comprises some buttons and some levers used for a user's inputting to carry out some determined functions. The reference light power circuit 25 and the exciting light control circuit 26 are started based on an input to the input unit 57.

As described above, the reference light or the exciting light is incident on the incident end 51a of the light guide 51. The light transmitted to the out end 51b of the light guide 51 illuminates a peripheral area nearby the head end of the insert tube 52 through a diffuser lens 54.

An optical image of the required object illuminated by the light is captured by the imaging device 53 through an object lens 55 and an exciting light cut-off filter 56. An optical image comprises reflected reference light components when the required object is illuminated by the reference light. The reflected reference light components of the optical image are captured by the imaging device 53. On the other hand, an optical image comprises reflected exciting light components and autofluorescence components when the required object is illuminated by the exciting light. The reflected exciting light components of the optical image are excluded by the exciting light cut-off filter 56. And then only the autofluorescence components of the optical image are captured by the imaging device 53.

The imaging device 53 is controlled by the imaging device driving circuit 41 so that the imaging device 53 captures the optical image of one field at least while the required object is continuously illuminated by the reference light. Or the imaging device 53 is controlled by the imaging device driving circuit 41 so that the imaging device 53 captures the optical image of one field at least while the required object is illuminated by the exciting light.

The image process system 34 comprises the first signal processing circuit 35a, a second signal processing circuit 35b, a histogram circuit 37, and first and second memories 39a, 39b.

The imaging device 53 is connected to the first signal processing circuit 35a. An image signal generated by the imaging device 53 is received by the first signal processing circuit 35a. The first signal processing circuit 35a carries out the predetermined signal processes, for example a white balance process, gamma correction process, and so on for the image signal. In addition, the analog image signals are converted to digital image data.

The first signal processing circuit 35a is connected to the timing controller 40. The timing controller 40 repeatedly and reciprocally outputs a reference timing signal and an exciting timing signal. The reference timing signal is output at the same time the reference light is controlled to pass through the shutter 27. The exciting timing signal is output at the same time the exciting light source 23 is switched on.

The first signal processing circuit 35a recognizes the image signal, generated while receiving the reference timing signal, as a reference image signal. The reference image signal corresponds to a reference image that is captured while the required object is illuminated by the reference light. On the other hand, the first signal processing circuit 35a recognizes the image signal, generated while receiving the exciting timing signal, as an autofluorescence image signal. The autofluorescence image signal corresponds to an autofluorescence image that is captured while the required object is illuminated by the exciting light.

The first signal processing circuit 35a is connected to the first and the second memories 39a and 39b. The reference image data, corresponding to the reference image signal, is stored in the first memory 39a. The autofluorescence image data, corresponding to the autofluorescence image signal, is stored in the second memory 39b. The first and second memories 39a and 39b are connected to the timing controller 40. The timing controller 40 controls the timing for storing the reference image data and the autofluorescence image data respectively in the first and second memories 39a and 39b.

In addition, the first signal processing circuit 35a is also connected to the histogram circuit 37. The autofluorescence image data is sent to the histogram circuit 37. The histogram circuit 37 generates an autofluorescence histogram data based on the autofluorescence image data. The autofluorescence histogram data corresponds to a histogram of luminance for the autofluorescence image, hereinafter referred to as Haf (reference to as Haf in FIG. 3).

The histogram circuit 37 is connected to the second signal processing circuit 35b. The autofluorescence histogram data is sent to the second signal processing circuit 35b. In addition, the second signal processing circuit 35b is connected to the first and second memories 39a and 39b. One of the reference image data and the autofluorescence image data, or both the reference image data and the autofluorescence image data are sent to the second signal processing circuit 35b.

The second signal processing circuit 35b carries out the AGC process. In the AGC process, an autofluorescence gain, that is an amplifying rate for brightening the autofluorescence image, is calculated based on the Haf. And then the second signal processing circuit 35b carries out an amplification process for the autofluorescence image data.

The calculation of the autofluorescence gain is carried out according to one of a max-mode and an average-mode. In the max-mode, the autofluorescence gain is calculated based on a maximum luminance of the autofluorescence image. On the other hand, the autofluorescence gain is calculated based on an average luminance of the autofluorescence image in the average-mode. A max-mode or an average-mode is selected when a user inputs an appropriate command to the input unit 57.

Figure 3:
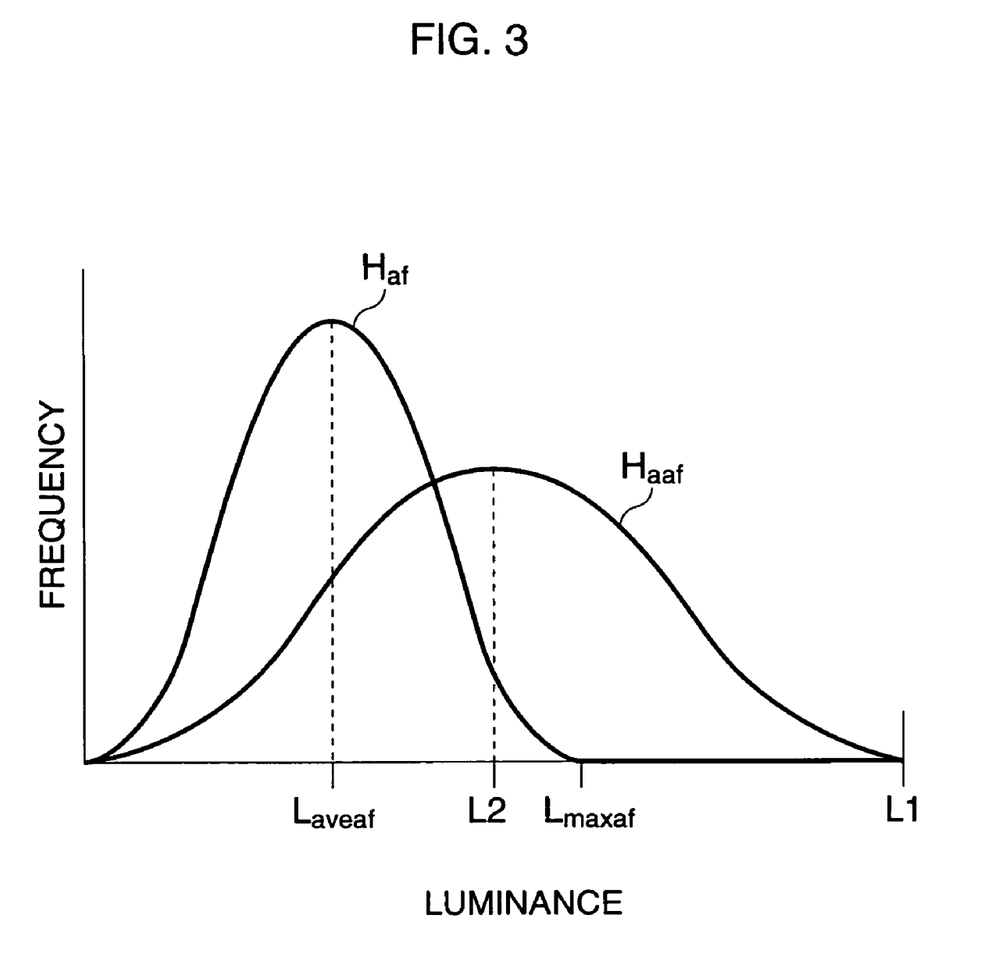
FIG. 3 is a histogram of luminance in an autofluorescence image and an amplified autofluorescence image.

A maximum luminance, hereinafter referred to as Lmaxaf, is detected from the Haf when the max-mode is selected. And then, the autofluorescence gain, that makes the Lmaxaf agree with a first luminance, hereinafter referred to as L1, is calculated by dividing the L1 by the Lmaxaf. The L1 is predetermined and stored in a ROM (not depicted). The L1 may be any adequate value. It may be determined so that the autofluorescence image brightened with the autofluorescence gain, calculated with the Lmaxaf and the L1, does not have white blurring, like halation. For example, the L1 is a maximum luminance value of which light can be displayed on the connected monitor 60.

An average luminance, hereinafter referred to as Laveaf, is calculated from the Haf when the average-mode is selected. And then, the autofluorescence gain, that makes the Laveaf agree with a second luminance, hereinafter referred to as L2, is calculated by dividing the L2 by the Laveaf. The L2 is predetermined and stored in the ROM. The L2 may be any adequate value. It may be determined so that the autofluorescence image brightened with the autofluorescence gain, calculated with the Laveaf and the L2, does not have white blurring, like halation. For example, the L2 is a half of a maximum luminance value of which light can be displayed on the connected monitor 60.

As described above, the amplification process is carried out for the autofluorescence image data after a calculation of the autofluorescence gain. In the amplification process, amplified autofluorescence image data is generated by amplifying the autofluorescence image data by the autofluorescence gain. Accordingly, an amplified autofluorescence image, corresponding to the amplified autofluorescence image data, is brighter than the autofluorescence image, as shown by a histogram of luminance for the amplified autofluorescence image (referred to as Haaf in FIG. 3).

Further, a user can finely adjust the autofluorescence gain by an input to the input unit 57. The amplification process is carried out by replacing the autofluorescence gain with the finely adjusted autofluorescence gain if there is an input to the input unit 57 for the fine adjustment.

Further, the second signal processing circuit 35b carries out a D/A conversion process and then the amplified autofluorescence image data, which is a digital image data, is converted to analog image signal. The second signal processing circuit 35b carries out some predetermined signal processes, for example a clamp process and a blanking process after the D/A conversion. Finally, an amplified autofluorescence image signal is generated.

The second signal processing circuit 35b is connected to the monitor 60. The second signal processing circuit 35b outputs the amplified autofluorescence image signal to the monitor 60. The amplified autofluorescence image is displayed over the whole display surface on the monitor 60.

In addition, the second signal processing circuit 35b can carry out a D/A conversion process and the predetermined signal processes for the reference image data. A reference image signal, that is converted from the reference image data, is sent to the monitor 60. And then the reference image is displayed on the monitor 60.

Figure 4:
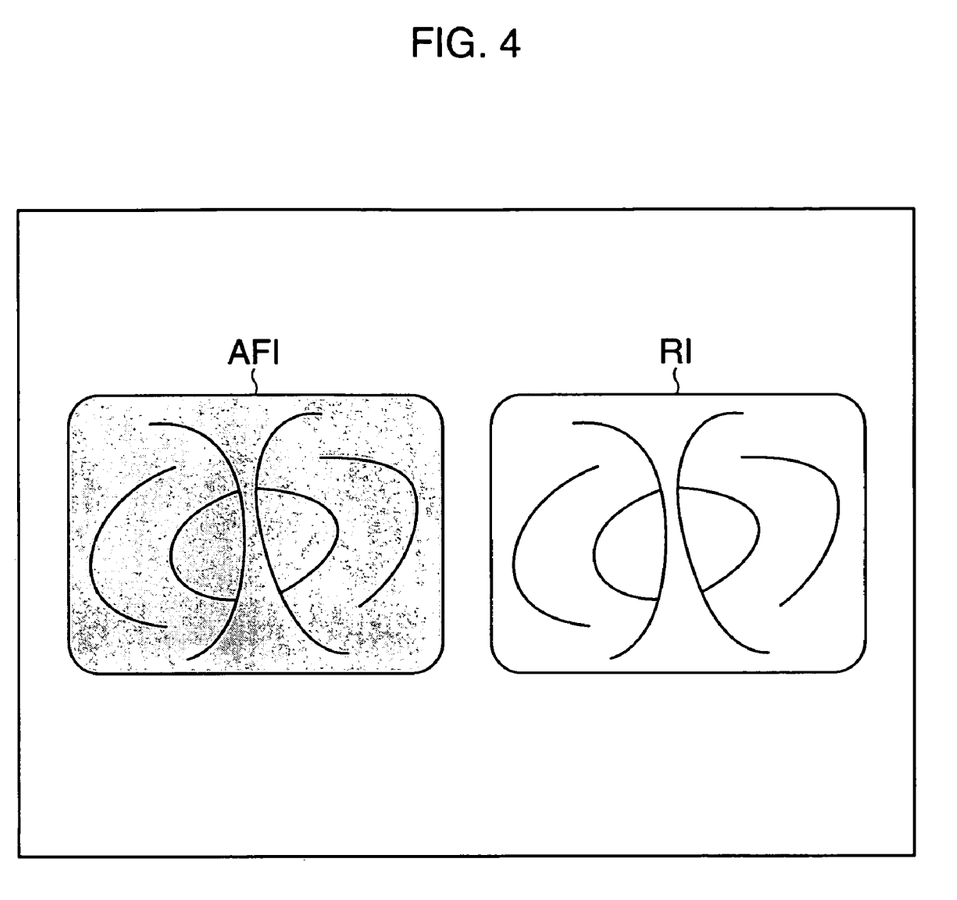
FIG. 4 illustrates an amplified autofluorescence image and a reference image displayed on a monitor simultaneously.
Figure 5:
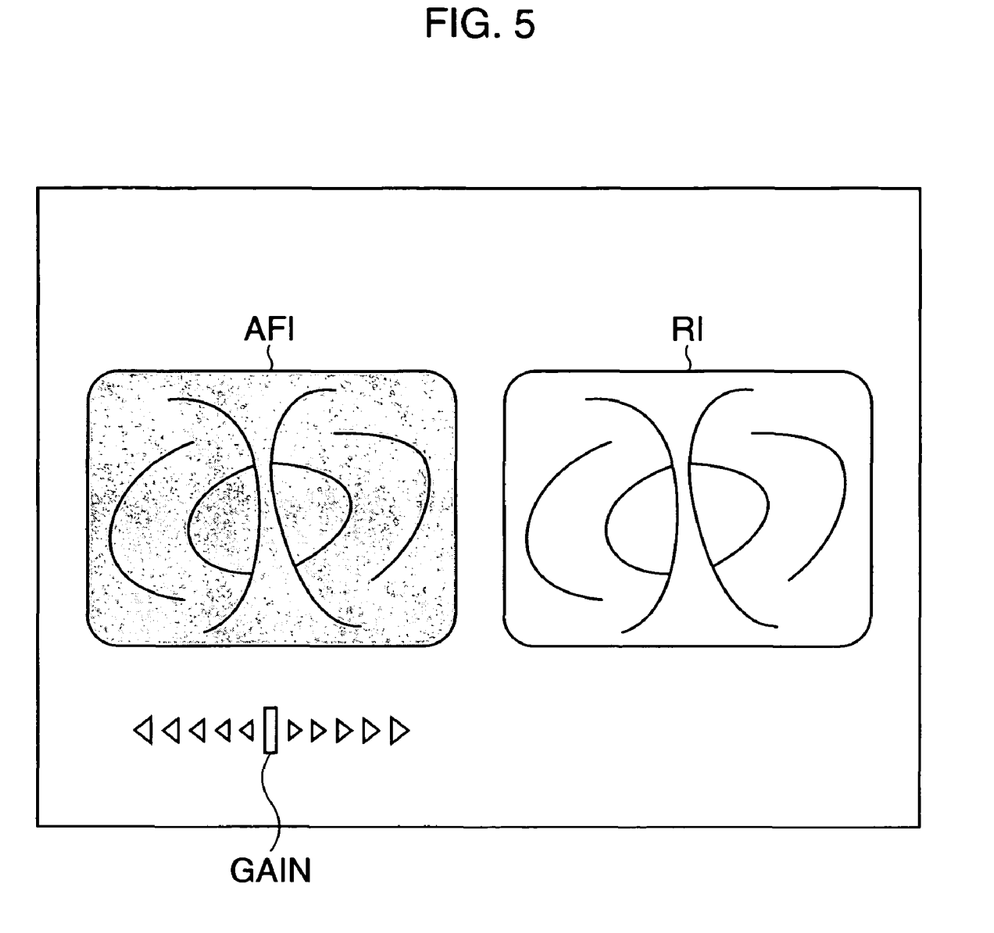
FIG. 5 illustrates the amplified autofluorescence image, the reference image, and the gain displayed on the monitor simultaneously.

The image displayed on the monitor 60 can be selected from the reference image and the amplified autofluorescence image when a user inputs an appropriate command to the input unit 57 (or processor surface). Or both of the images can be displayed simultaneously as shown in FIG. 4. In FIG. 4, the reference image and the amplified autofluorescence image are respectively referred to as RI, and AFI. Further, the autofluorescence gain can be displayed on the monitor 60 when a user inputs an appropriate command to the input unit 57 as shown in FIG. 5.

In the case where both of the images and the autofluorescence gain are displayed, the second signal processing circuit 35b carries out allocation of area to display each image, and scales down each image. The second signal processing circuit 35b is connected to the timing controller 40. The allocation of the areas and the scaling down of each image are carried out based on a timing signal output from the timing controller 40.

Next, timings for illuminating the reference light or exciting light, for carrying out the AGC process, and so on, are explained below using the timing chart of FIG. 6.

The timing controller 40 outputs a field signal to the exciting light control circuit 26, the shutter circuit 32, the first signal processing circuit 35a, the second signal processing circuit 35b, the first memory 39a, and the second memory 39b. The field signal is a rectangular wave having high and low states. The high and low states change repeatedly and cyclically.

Figure 6:
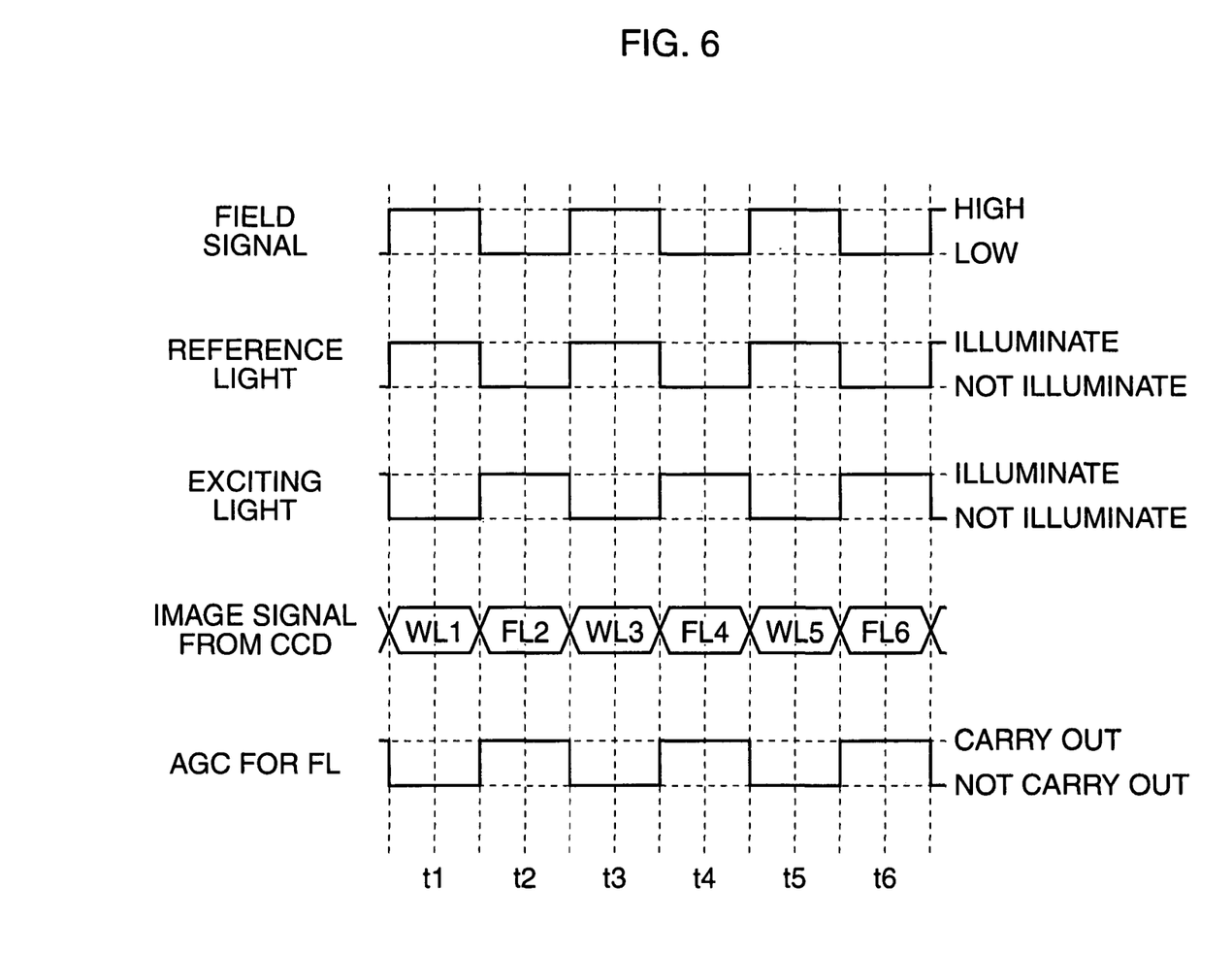

The shutter 27 is driven by the shutter circuit 32 so that the reference light can pass through the shutter 27 while the field signal is in the high state as shown by the timings t1, t3, and t5 of FIG. 6. And during the same period, the exciting light control circuit 26 switches off the exciting light source 23. Consequently, the reference light illuminates a required object.

Further, the imaging device 53 generates reference image signals, for example WL1, WL3, WL5 of FIG. 6, during the same period. Further the AGC process is not carried out at the second signal processing circuit 35b during the same period as shown in AGC for FL of FIG. 6. Consequently, the predetermined signal processes without the AGC process are carried out for the reference image data, that is input to the second signal processing circuit 35b through the first signal processing circuit 35a and the first memory 39a during this period.

On the other hand, the exciting light control circuit 26 switches on the exciting light source 23 while the field signal is in the low state as shown by the timings t2, t4, and t6 of FIG. 6. And during the same period, the shutter 27 is driven by the shutter circuit 32 so that the reference light can be shielded. Consequently, the exciting light illuminates a required object.

Further, the imaging device 53 generates autofluorescence image signals, for example FL2, FL4, and FL6 of FIG. 6, during the same period. Further the AGC process is carried out in the second signal processing circuit 35b during the same period as shown in AGC for FL of FIG. 6. Consequently, the AGC process and the predetermined signal processes are carried out for the autofluorescence image data, that is input to the second signal processing circuit 35b through the first processing circuit 35a and the second memory 39b during this period.

The field signal sent to the exciting light control circuit 26 corresponds to the emission timing signal described above. And the field signal sent to the shutter circuit 32 corresponds to the shutter timing signal described above.

The image signal, that is sent to the first signal processing circuit 35a from the imaging device 53 while the field signal is in the high state, is recognized as the reference image signal. On the other hand, the image signal, that is sent to the first signal processing circuit 35a from the imaging device 53 while the field signal is in the low state, is recognized as the autofluorescence image signal.

The first memory is driven so that the first memory stores the reference image data, that is output from the first signal processing circuit 35a during the high state of the field signal. Consequently, the high state of the field signal corresponds to the reference timing signal described above. On the other hand, the second memory is driven so that the second memory stores the autofluorescence image data, that is output from the first signal processing circuit 35b during the low state of the field signal. Consequently, the low state of the field signal corresponds to the exciting timing signal described above.

Figure 7:
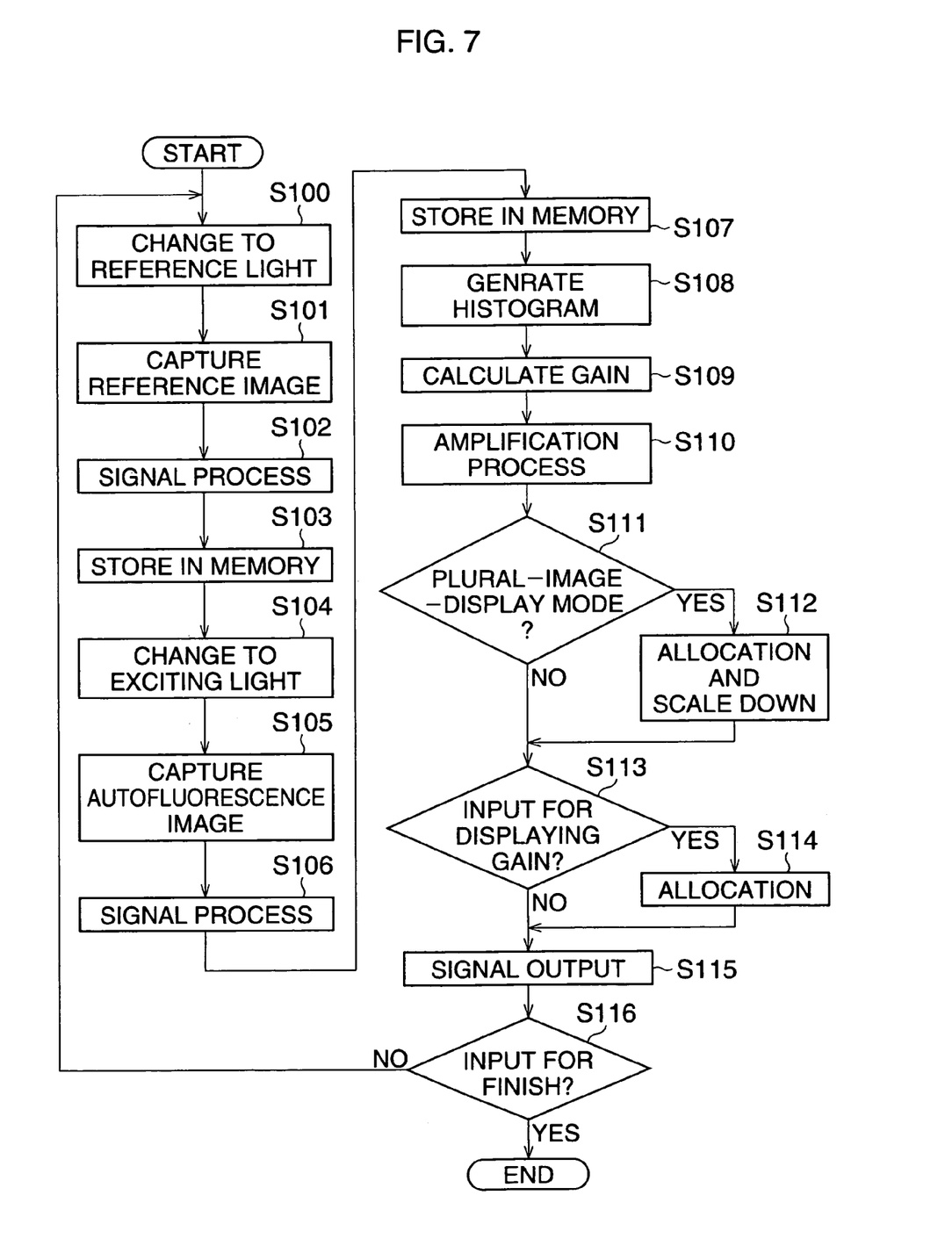
FIG. 7 is a flowchart to explain the control process and the image data process.

Next, control processes and image signal processes carried out by the endoscope processor 20 are explained below using the flowchart of FIG. 7.

The control processes and the image signal processes of this embodiment start when a user inputs an appropriate command to the input unit 57 for displaying an amplified autofluorescence image on the monitor 60. At step S100, the shutter timing signal is output to the shutter circuit 32 so that the shutter is driven to insert the aperture 27o into the optical path of the reference light. Further, the emission timing signal for switching off the exciting light is output to the exciting light control circuit 26. Then the light to illuminate a required object is changed to the reference light by driving the shutter 27.

At step S101, the imaging device 53 is driven to capture the optical image of the required object that is illuminated by the reference light. And then the process goes to step S102. At step S102, the predetermined signal processes, including the A/D conversion processes, are carried out for the reference image signal generated by the imaging device 53. The reference image signal, which is analog, is converted to digital reference image data by the predetermined processes.

At step S103, the reference image data is stored in the first memory 39a, and then the process goes to step S104. At step S104, the emission timing signal for emitting the exciting light is output to the exciting light control circuit 26. Then the exciting light control circuit 26 makes the exciting light source 23 emit the exciting light. Further, the shutter timing signal is output to the shutter circuit 32 so that the shutter is driven to insert the shielding plate 27s into the optical path of the reference light. Then the light to illuminate a required object is changed to the exciting light.

At step S105, the imaging device 53 is driven to capture the optical image of the required object that is illuminated by the exciting light. The predetermined signal processes, including the A/D conversion process, are carried out for the autofluorescence image signal generated by the imaging device 53. Then the analog autofluorescence image signal is converted to digital autofluorescence image data by predetermined processes at step S106.

At step S107, the autofluorescence image data is stored in the second memory 39b. At next step S108, the autofluorescence histogram data is generated based on the autofluorescence image data. After generating the autofluorescence histogram data, the process goes to step S109.

At step S109, the autofluorescence gain, that is the amplifying rate for brightening the autofluorescence image, is calculated based on the Haf and one of the L1 and the L2. The Lmaxaf is detected from the Haf when the max-mode is selected. And then, the autofluorescence gain for the max-mode, that makes the Lmaxaf agree with the L1, is calculated. The Laveaf is calculated from the Haf when the average-mode is selected. And then, the autofluorescence gain for the average-mode, that makes the Laveaf agree with the L2, is calculated.

At the next step S110, the amplified autofluorescence image data is generated by amplifying the autofluorescence image data with the autofluorescence gain calculated at step S109, then the process goes to step S111.

At step S111, it is judged whether a plural-image-displaying mode, where the reference image is displayed with the amplified autofluorescence image, is selected or not. The process goes to step S112 when the plural-image-display mode is selected. At step S112, allocation of areas to display each image, and the scaling down of each image are carried out, then the process goes to step S113. Or the process goes to step S113 after carrying out the predetermined processes, excepting for the allocation and scaling down, for the amplified autofluorescence image data, when the plural-image-display mode is not selected.

At step S113, it is determined whether a user has input the appropriate command to the input unit 57 for displaying the autofluorescence gain or not. The process goes to step S114 when there is the appropriate input at step S113. At step S114, allocation of area to display the autofluorescence gain is carried out, then the process goes to step S115. Or the process goes to step S115 when there is no appropriate input.

At step S115, the amplified autofluorescence image signal or a complex image signal, corresponding to an image separately including the amplified autofluorescence image and the reference image, is output to the monitor 60.

At the next step S116, it is judged whether the user has input an appropriate command to finish displaying the amplified autofluorescence image. When there is the appropriate input, the control processes and the image signal processes are completed. On the other hand, the process returns to step S100 when there is no appropriate input. The processes from step S100 to step S116 are repeated until there is an appropriate input for finishing.

In the above embodiment, the autofluorescence gain is automatically calculated to be an adequate value and the autofluorescence image data is amplified by the autofluorescence gain. Consequently, it is possible to automatically make the autofluorescence image adequately bright without user's control.

Further in the above embodiment, it is possible to display the reference image with the amplified autofluorescence image on the monitor 60. Consequently, a user can observe the reference image without changing between the reference image and the amplified autofluorescence image.

Further in the above embodiment, it is possible to finely adjust the autofluorescence gain. Consequently, a user can preferably adjust brightness of the amplified autofluorescence image even if there is some noticeable noise in the amplified autofluorescence image or the amplified autofluorescence image is still dark.

Further in the above embodiment, it is possible to display the autofluorescence gain on the monitor 60. Consequently, a user can be aware of the autofluorescence gain, which can contribute to an accurate diagnosis.

The AGC process is carried out only for the autofluorescence image data in the above embodiment. However, it is possible to carry out additional AGC processes for the reference image data according the gain calculated based on the histogram for the reference image and to output the amplified reference image data to the monitor 60.

In the transformed embodiment, the reference image data is sent to the histogram circuit 37 and reference histogram data of the reference image is generated based on the reference image data. The reference histogram data corresponds to a histogram of luminance for the reference image. The second image signal processing circuit 35b calculates a reference gain based on the histogram of luminance for the reference image and carries out an AGC process for the reference image. The reference gain is used for amplifying the reference image data.

Figure 8:
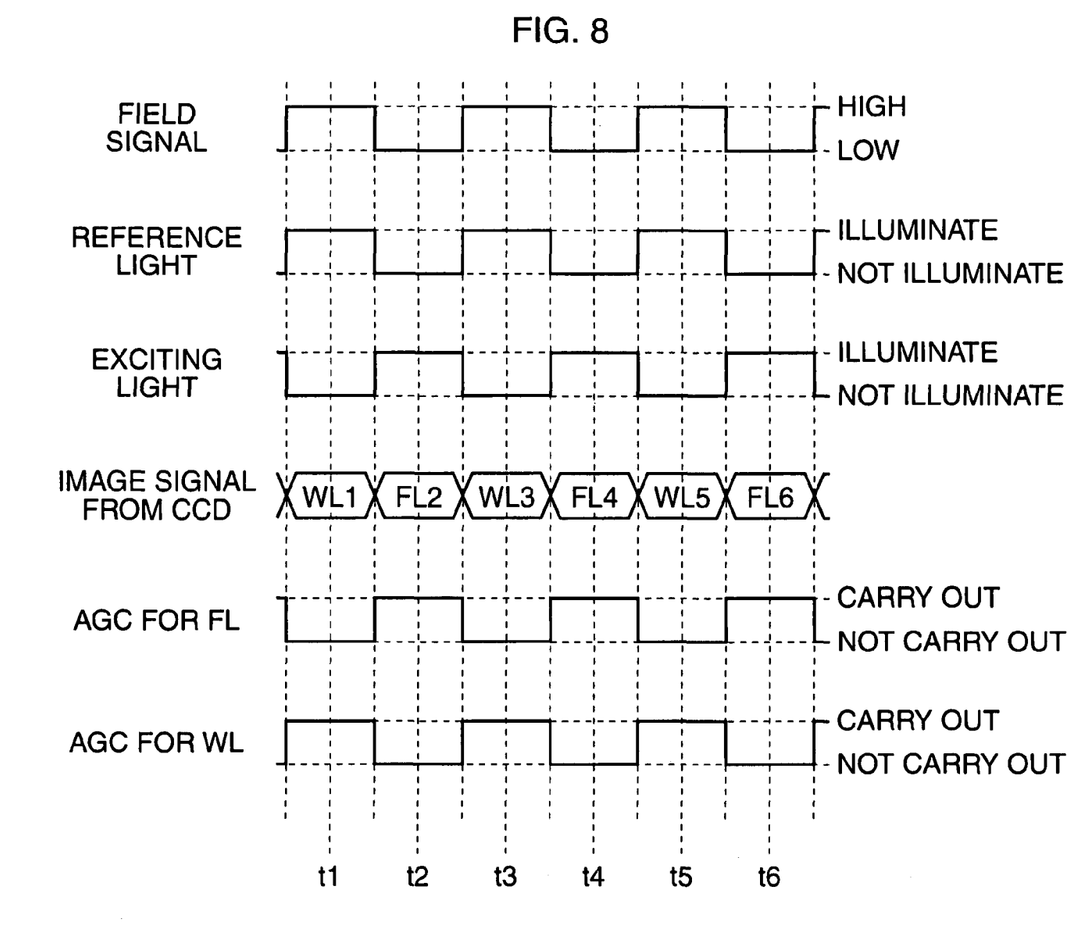
FIG. 8 is a timing chart to explain a timing to illuminate reference light or exciting light, to carry out the auto gain control process, and so on in the transformed embodiment.

In the transformed embodiment, the AGC process is carried out at the second signal processing circuit 35b while the field signal is in the high state as shown in AGC for WL of FIG. 8. Consequently, the AGC process and the predetermined signal processes are carried out for the reference image data, that is input to the second signal processing circuit 35b through the first processing circuit 35a and the first memory 39a during this period.

In the transformed embodiment, it is possible to make the reference image, displayed on the monitor 60, adequately bright when the reference image is dark even if the aperture is fully opened. In addition, it is possible to control brightness of the reference image by the AGC process more quickly than by the control of light irradiation with a mechanical aperture like the diaphragm 28. Consequently, the brightness of the reference image can be more stable. And it is easy to control the brightness of the reference image until the diaphragm 28 is stably driven.

The L1 is a single predetermined value and the L2 is a single predetermined value in the above embodiment. However, they may change according to an endoscope 50 connected to the endoscope processor 20. For example, an endoscope has a memory to store the L1 and the L2, that are predetermined according to the properties of the endoscope. And the endoscope processor 20 reads the L1 or the L2 stored in the memory for a gain calculation. Or the ROM stores some predetermined luminance values, that are decided according to the properties of the endoscopes expected to be connected to the endoscope processor 20. And one of the predetermined luminance values stored in the ROM is selected as the L1 or the L2 according to an endoscope connected to the endoscope processor 20. The brightness of the amplified autofluorescence image can be controlled to be suitable for a connected endoscope due to using an adequate luminance value for the L1 or the L2, according to an endoscope. For example, a lower luminance value is used as the L1 or the L2 when a bronchus endoscope or an endoscope for the large intestines is connected to the endoscope processor 20. This is because a gain used for the amplification process is smaller since a lumen of a bronchus or large intestines is narrow. A higher luminance value is used as the L1 or the L2 when an endoscope for an upper digestive tract is connected to the endoscope processor 20. This is because a gain used for the amplification process is larger since a lumen of an upper digestive tract is wide.

It is described as an example in the above embodiment that the L1 and the L2 are respectively fixed values in the amplified autofluorescence image. However, the L1 or the L2 can be finely adjusted. It might not be a problem to observe the area where a user wants to look at even if a little halation appears in the amplified autofluorescence image due to diffused reflection at a mucous membrane. The amplified autofluorescence image displayed on the monitor 60 may be observable for a user even if the L1 is finely adjusted within the decided range. For example, the L1 or the L2 can be finely adjusted within a range between 0% and +5%. Conversely, the L1 or the L2 can be finely adjusted within a range between −5% and 0%.

The autofluorescence gain is calculated based on the Lmaxaf or the Laveaf for an autofluorescence image captured by the imaging device for one field of image data in the above embodiment. However, it is possible to calculate the autofluorescence gain based on the average of the Lmaxafs or the Laveafs in some autofluorescence images captured by the imaging device at different times. The amount of exciting light emitted by the exciting light source 23 may swing, resulting in changing of brightness of the amplified autofluorescence image. However, the swinging of brightness of the amplified autofluorescence image can be lowered owing to using the gain calculated based on the average of the Lmaxafs or the Laveafs in some autofluorescence images captured at different timings. Further, the brightness of the amplified reference image may swing, however the swinging of brightness of the amplified reference image can be lowered in the same way.

Figure 9:
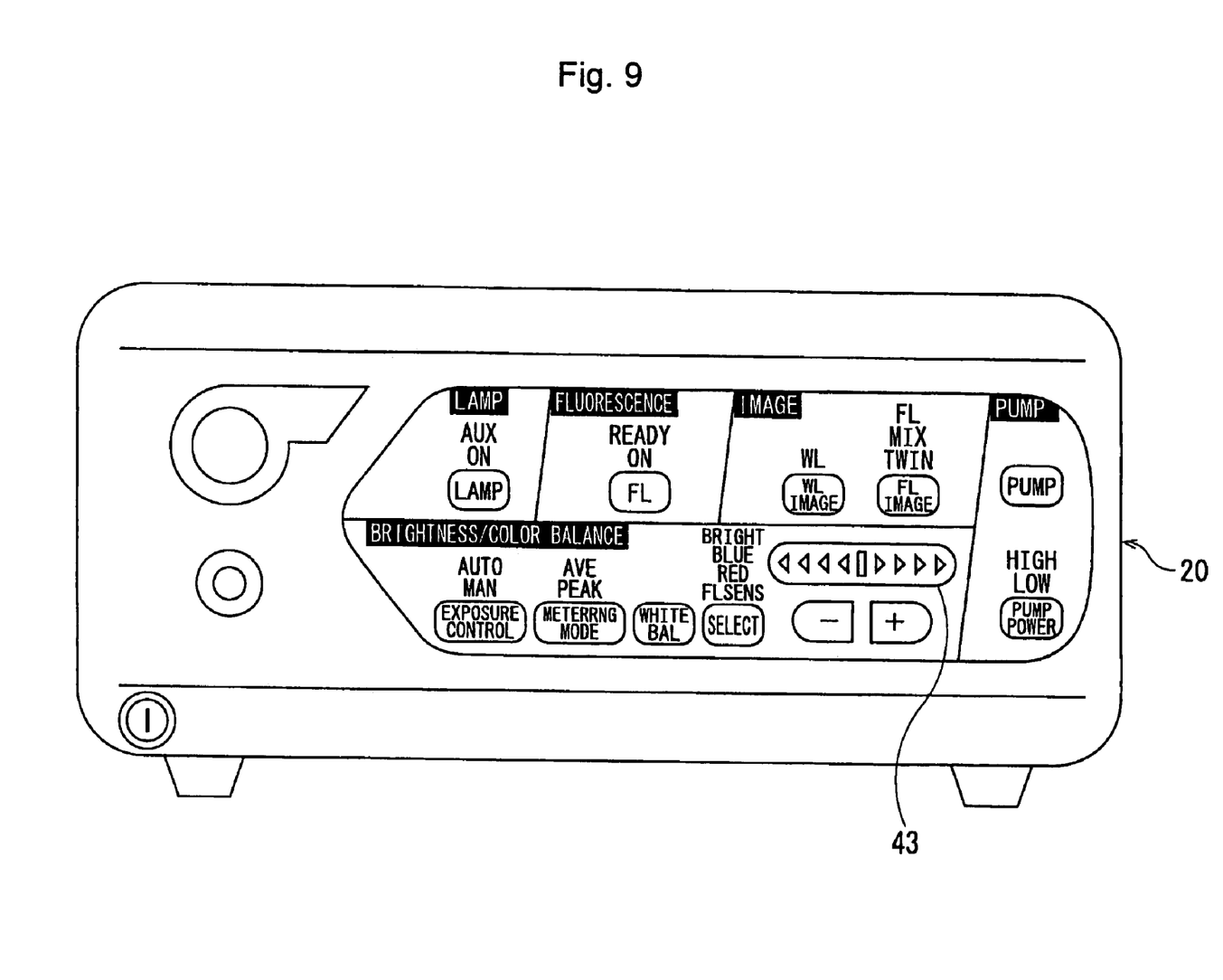
FIG. 9 shows the control surface of the endoscope processor.

The autofluorescence gain is displayed on the monitor 60 in the above embodiment. However, the autofluorescence gain can be displayed on a gain-monitor 43 mounted on the control surface of the endoscope processor 20 as shown in FIG. 9.

The above embodiment can be implemented by installing a program for the AGC process in an all purpose image data processor, which can be connected to the reference and exciting light sources.

Although the embodiments of the present invention have been described herein with reference to the accompanying drawings, obviously many modifications and changes may be made by those skilled in this art without departing from the scope of the invention.

The present disclosure relates to subject matter contained in Japanese Patent Application No. 2005-039029 (filed on Feb. 16, 2005), which is expressly incorporated herein, by reference, in its entirety.

The invention claimed is:

1. An image data processor, comprising:
an image signal receiver that receives an autofluorescence image signal generated by an imaging device when said imaging device captures an autofluorescence image, the autofluorescene image being an optical image of an object illuminated by an exciting light that makes an organ generate autofluorescence;
a histogram generator that generates an autofluorescence histogram, the autofluorescence histogram being a histogram of luminance in said autofluorescence image based on said autofluorescence image signal;
a gain calculator that calculates an autofluorescence gain used for amplifying said autofluorescence image signal based on said autofluorescence histogram and a predetermined luminance value for said autofluorescence image signal, wherein said autofluorescence gain is calculated so that one of an average luminance value and a maximum luminance value in said autofluorescence histogram amplified by said autofluorescence gain corresponds to said predetermined luminance value;
an amplifier that generates an amplified autofluorescence image signal by amplifying said autofluorescence image signal by said autofluorescence gain; and
a signal feeder that can output said amplified autofluorescence image signal to a monitor that displays an amplified autofluorescence image corresponding to said amplified autofluorescence image signal.

2. An image data processor according to claim 1, further comprising a gain-monitor that displays said autofluorescence gain.

3. An image data processor according to claim 1, wherein said autofluorescence gain can be displayed on said monitor.

4. An image data processor according to claim 1, wherein said imaging device generates a reference image signal when said imaging device captures a reference image, the reference image being an optical image of an object illuminated by a reference light, and said reference image and said autofluorescence image can be simultaneously displayed on said monitor.

5. An image data processor according to claim 1, wherein
said image signal receiver receives a reference image signal generated by said imaging device when said imaging device captures a reference image, the reference image being an optical image of an object illuminated by a reference light,
said histogram generator generates a reference histogram, the reference histogram being a histogram of luminance in said reference image based on said reference image signal,
said gain calculator calculates a reference gain used for amplifying said reference image signal based on said reference histogram and a predetermined luminance value for said reference image signal,
said amplifier generates an amplified reference image signal by amplifying said reference image signal by the reference gain, and
said signal feeder outputs said amplified reference image signal to the monitor.

6. An image data processor according to claim 1, wherein said gain calculator calculates said autofluorescence gain based on a plurality of said autofluorescence histograms, that are generated based on a plurality of said autofluorescence image signals generated at different times.

7. The image data processor according to claim 1, the predetermined luminance value comprising a value distinct from a luminance of an optical image of an object generated by the imaging device.

8. The image data processor according to claim 1, the predetermined luminance value comprising one of a maximum luminance value and half a maximum luminance value of light displayable on the monitor.

9. A non-transitory computer readable medium that stores a program executable by a computer, the computer readable medium comprising:
an image signal receiving segment that receives an autofluorescence image signal generated by an imaging device when the imaging device captures an autofluorescence image, the autofluorencence image being an optical image of an object illuminated by an exciting light that makes an organ generate autofluorescence;
a histogram generating segment that generates an autofluorescence histogram, the autofluorencence histogram being a histogram of luminance in the autofluorescence image based on the autofluorescence image signal;
a gain calculating segment that calculates an autofluorescence gain used for amplifying the autofluorescence image signal based on the autofluorescence histogram and a predetermined luminance value, wherein the autofluorescence gain is calculated so that one of an average luminance value and a maximum luminance value in the autofluorescence histogram amplified by the autofluorescence gain corresponds to the predetermined luminance value;
an amplifying segment that generates an amplified autofluorescence image signal by amplifying the autofluorescence image signal by said the autofluorescence gain; and
a signal feeding segment that can output the amplified autofluorescence image signal to a monitor that displays an amplified autofluorescence image corresponding the amplified autofluorescence image signal.

10. The non-transitory computer readable medium according to claim 9,
the predetermined luminance value comprising a value distinct from a luminance of an optical image of an object generated by the imaging device.

11. An electronic endoscope system, comprising:
an electronic endoscope having an imaging device that generates an autofluorescence image signal when said imaging device captures an autofluorescence image, the autofluorescence image being an optical image of an object illuminated by an exciting light that makes an organ generate autofluorescence;
a histogram generator that generates an autofluorescence histogram, the autofluorescence histogram being a histogram of luminance in said autofluorescence image based on said autofluorescence image signal;
a gain calculator that calculates an autofluorescence gain used for amplifying said autofluorescence image signal based on said autofluorescence histogram and a predetermined luminance value, wherein said autofluorescence gain is calculated so that one of an average luminance value and a maximum luminance value in said autofluorescence histogram amplified by said autofluorescence gain corresponds to said predetermined luminance value;

an amplifier that generates an amplified autofluorescence image signal by amplifying said autofluorescence image signal by said autofluorescence gain; and a monitor that displays said amplified autofluorescence image corresponding to said amplified autofluorescence image signal.

12. The electronic endoscope system according to claim 11, wherein said imaging device is mounted in an endoscope, and said predetermined luminance value is determined in accordance with properties of said endoscope.

13. The electronic endoscope system according to claim 11, further comprising an input unit that manually adjusts said autofluorescence gain calculated by said gain calculator.

14. The electronic endoscope system according to claim 11;

the predetermined luminance value comprising a value distinct from a luminance of an optical image of an object generated by the imaging device.

15. An image data processor comprising:

an image signal receiver that receives an autofluorescence image signal generated by an imaging device when said imaging device captures an autofluorescence image, the autofluorescence image being an optical image of an object illuminated by an exciting light that makes an organ generate autofluorescence;

a histogram generator that generates an autofluorescence histogram, the autofluorescence histogram being a histogram of luminance in said autofluorescence image based on said autofluorescence image signal;

a gain calculator that calculates an autofluorescence gain used for amplifying said autofluorescence image signal based on said autofluorescence histogram and a predetermined luminance value for said autofluorescence image signal, wherein said autofluorescence gain is calculated so that one of a maximum luminance value and an average luminance value in said autofluorescence histogram amplified by said autofluorescence gain corresponds to said predetermined luminance value;

an amplifier that generates an amplified autofluorescence image signal by amplifying said autofluorescence image signal by said autofluorescence gain; and a signal feeder that can output said amplified autofluorescence image signal to a monitor that displays an amplified autofluorescence image corresponding to said amplified autofluorescence image signal, wherein said imaging device is mounted in an endoscope, and said predetermined luminance value is determined in accordance with properties of the endoscope.

16. The image data processor according to claim 15, further comprising a gain-monitor that displays said autofluorescence gain.

17. The image data processor according to claim 15, the predetermined luminance value comprising a value distinct from a luminance of an optical image of an object generated by the imaging device.

18. An image data processor, comprising:

an image signal receiver that receives an autofluorescence image signal generated by an imaging device when said imaging device captures an autofluorescence image, the autofluorescence image being an optical image of an object illuminated by an exciting light that makes an organ generate autofluorescence;

a histogram generator that generates an autofluorescence histogram, the autofluorescence histogram being a histogram of luminance in said autofluorescence image based on said autofluorescence image signal;

a gain calculator that calculates an autofluorescence gain used for amplifying said autofluorescence image signal based on said autofluorescence histogram and a predetermined luminance value for said autofluorescence image signal, wherein said autofluorescence gain is calculated so that one of a maximum luminance value and an average luminence value in said autofluorescence histogram amplified by said autofluorescence gain corresponds to said predetermined luminance value;

an input unit that manually adjusts said autofluorescence gain calculated by said gain calculator;

an amplifier that generates an amplified autofluorescence image signal by amplifying said autofluorescence image signal by said autofluorescence gain; and a signal feeder that can output said amplified autofluorescence image signal to a monitor that displays an amplified autofluorescence image corresponding to said amplified autofluorescence image signal.

19. An image data processor according to claim 18, further comprising a gain-monitor that displays said autofluorescence gain.

20. The image data processor according to claim 18, the predetermined luminance value comprising a value distinct from a luminance of an optical image of an object generated by the imaging device.

* * * * *